(12) United States Patent
Crowley

(10) Patent No.: US 8,126,531 B2
(45) Date of Patent: Feb. 28, 2012

(54) MINIATURE SPECTROMETER

(75) Inventor: Robert J. Crowley, Sudbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1964 days.

(21) Appl. No.: 10/022,965

(22) Filed: Dec. 13, 2001

(65) Prior Publication Data

US 2002/0115918 A1 Aug. 22, 2002

Related U.S. Application Data

(63) Continuation of application No. 09/478,774, filed on Jan. 6, 2000, now Pat. No. 6,343,227, which is a continuation of application No. 08/898,604, filed on Jul. 22, 1997, now Pat. No. 6,119,031.

(60) Provisional application No. 60/033,334, filed on Nov. 21, 1996.

(51) Int. Cl.
*A61B 5/05* (2006.01)

(52) U.S. Cl. ........ 600/407; 600/310; 600/341; 600/476; 600/473; 600/325; 600/477; 600/332; 600/479

(58) Field of Classification Search .................. 600/407, 600/410, 473, 476, 310, 110, 160, 478, 342, 600/100; 607/88, 92
See application file for complete search history.

(56) References Cited

U.S. PATENT DOCUMENTS

| | | | |
|---|---|---|---|
| 2,002,559 A | 5/1935 | Wappler | 174/39 |
| 2,583,937 A | 1/1952 | Fessati | 128/4 |
| 3,176,114 A | 3/1965 | Kneisley | 219/223 |
| 4,075,475 A | 2/1978 | Risby et al. | |
| 4,233,493 A | 11/1980 | Nath | 219/354 |
| 4,274,706 A | 6/1981 | Tangonan | 350/96.19 |
| 4,289,966 A | 9/1981 | Roberts | 250/378 |
| 4,340,307 A | 7/1982 | Diamond et al. | 356/418 |
| 4,472,728 A | 9/1984 | Grant et al. | 357/30 |
| 4,541,272 A | 9/1985 | Bause | 73/118 |
| 4,548,505 A | 10/1985 | Ono | 356/445 |
| 4,556,057 A | 12/1985 | Hiruma et al. | |
| 4,570,638 A | 2/1986 | Stoddart et al. | |
| 4,578,061 A | 3/1986 | Lemelson | |

(Continued)

FOREIGN PATENT DOCUMENTS

AU 199868650 B2 10/1998

(Continued)

OTHER PUBLICATIONS

Anidjar et al, ULIAD Btw Malignant and Normal Urothelial Cells and Tissues, Jul. 1996, Journal of Biomedical Optics p. 335-340.*

(Continued)

*Primary Examiner* — Brian Casler
*Assistant Examiner* — Joel Lamprecht
(74) *Attorney, Agent, or Firm* — Finnegan, Henderson, Farabow, Garrett & Dunner LLP

(57) ABSTRACT

A miniaturized spectrometer is adapted for placement within a body near tissue to be characterized. The spectrometer includes a light source and a plurality of light detectors. The light source generates light to illuminate the tissue. The detectors detect optical signals from the illuminated tissue and convert these optical signals to electrical signals. The miniaturized spectrometer can be disposed at the distal end of an interventional device. Optical conduits, such as fiber optic cables or strands, extending the length of the interventional device are not required when the miniature spectrometer is employed.

20 Claims, 3 Drawing Sheets

U.S. PATENT DOCUMENTS

| | | | |
|---|---|---|---|
| 4,672,972 A | 6/1987 | Berke | 128/653 |
| 4,718,417 A | 1/1988 | Kittrell et al. | 128/303.1 |
| 4,803,992 A | 2/1989 | Lemelson | |
| 4,872,458 A | 10/1989 | Kanshira et al. | 128/401 |
| 4,882,623 A | 11/1989 | Uchikubo | 358/98 |
| 4,894,547 A | 1/1990 | Leffell et al. | |
| 4,902,896 A | 2/1990 | Fertig, Sr. et al. | 290/348 |
| 4,928,172 A | 5/1990 | Uehara et al. | 358/98 |
| 4,930,516 A | 6/1990 | Alfano et al. | |
| 4,938,602 A | 7/1990 | May et al. | 356/435 |
| 4,981,138 A | 1/1991 | Deckelbaum et al. | 128/665 |
| 5,001,556 A | 3/1991 | Nakamura et al. | 358/98 |
| 5,009,655 A | 4/1991 | Daignault, Jr. et al. | 606/7 |
| 5,021,888 A | 6/1991 | Knodou et al. | 358/213.11 |
| 5,034,010 A | 7/1991 | Kittrell et al. | |
| 5,036,853 A | 8/1991 | Jeffcoat et al. | |
| 5,042,494 A | 8/1991 | Alfano | 128/665 |
| 5,045,056 A | 9/1991 | Behl | 604/49 |
| 5,056,503 A | 10/1991 | Nagasaki et al. | 128/6 |
| 5,062,428 A | 11/1991 | Chance | |
| 5,106,387 A | 4/1992 | Kittrell et al. | 606/15 |
| 5,115,137 A | 5/1992 | Andersson-Engels et al. | |
| 5,116,759 A | 5/1992 | Klainer et al. | 435/288 |
| 5,125,404 A | 6/1992 | Kittrell et al. | |
| 5,127,407 A | 7/1992 | Tan | 128/633 |
| 5,131,398 A | 7/1992 | Alfano et al. | 128/665 |
| 5,152,295 A | 10/1992 | Kobayashi et al. | |
| 5,166,755 A | 11/1992 | Gat | 356/419 |
| 5,172,693 A | 12/1992 | Doody | |
| 5,174,297 A | 12/1992 | Daikuzono | |
| 5,187,572 A | 2/1993 | Nakamura et al. | 358/98 |
| 5,187,672 A | 2/1993 | Chance et al. | |
| 5,193,542 A | 3/1993 | Missanelli et al. | |
| 5,197,470 A | 3/1993 | Helfer et al. | |
| 5,199,431 A | 4/1993 | Kittrell et al. | |
| 5,201,318 A | 4/1993 | Rava et al. | |
| 5,206,174 A | 4/1993 | Gehrke et al. | 436/58 |
| 5,213,569 A | 5/1993 | Davis | 604/22 |
| 5,233,621 A | 8/1993 | Lawandy | 372/22 |
| 5,242,437 A | 9/1993 | Everett et al. | 606/15 |
| 5,261,410 A | 11/1993 | Alfano et al. | |
| 5,262,645 A | 11/1993 | Lambert et al. | 250/339 |
| 5,280,788 A | 1/1994 | Janes et al. | |
| 5,304,173 A | 4/1994 | Kittrell et al. | 606/15 |
| 5,305,748 A | 4/1994 | Wilk | |
| 5,309,907 A | 5/1994 | Fang et al. | 128/633 |
| 5,318,024 A | 6/1994 | Kittrell et al. | 128/634 |
| 5,348,018 A | 9/1994 | Alfano et al. | |
| 5,350,375 A | 9/1994 | Deckelbaum et al. | 606/7 |
| 5,351,532 A | 10/1994 | Hager | 73/153 |
| 5,377,676 A | 1/1995 | Vari et al. | 128/634 |
| 5,383,467 A | 1/1995 | Auer et al. | |
| 5,386,827 A | 2/1995 | Chance et al. | |
| 5,398,844 A | 3/1995 | Zaslavsky et al. | 221/208 |
| 5,402,778 A | 4/1995 | Chance | |
| 5,402,792 A | 4/1995 | Kimura | 128/663.01 |
| 5,405,369 A | 4/1995 | Selman et al. | 607/88 |
| 5,413,108 A | 5/1995 | Alfano | |
| 5,417,207 A | 5/1995 | Young et al. | 128/634 |
| 5,419,323 A | 5/1995 | Kittrell et al. | |
| 5,421,337 A | 6/1995 | Richards-Kortum et al. | |
| 5,421,339 A | 6/1995 | Ramanujam et al. | |
| 5,445,608 A | 8/1995 | Chen et al. | 604/20 |
| 5,452,723 A | 9/1995 | Wu et al. | |
| 5,456,252 A | 10/1995 | Vari et al. | |
| 5,461,229 A | 10/1995 | Sauter et al. | 250/253 |
| 5,467,767 A | 11/1995 | Alfano et al. | 128/665 |
| 5,512,757 A | 4/1996 | Cederstrand et al. | |
| 5,517,313 A | 5/1996 | Colvin, Jr. | |
| 5,528,368 A * | 6/1996 | Lewis et al. | 356/456 |
| 5,542,928 A | 8/1996 | Evans et al. | 604/113 |
| 5,545,897 A | 8/1996 | Jack | |
| 5,553,614 A | 9/1996 | Chance | |
| 5,555,885 A | 9/1996 | Chance | |
| 5,556,421 A | 9/1996 | Prutchi et al. | 607/36 |
| 5,562,100 A | 10/1996 | Kittrell et al. | |
| 5,571,152 A | 11/1996 | Chen et al. | 607/92 |
| 5,579,773 A | 12/1996 | Vo-Dinh et al. | |
| 5,632,740 A | 5/1997 | Koch et al. | |
| 5,647,368 A | 7/1997 | Zeng et al. | 128/665 |
| 5,679,965 A * | 10/1997 | Schetzina | 257/103 |
| 5,686,734 A * | 11/1997 | Hamakawa et al. | 257/16 |
| 5,743,260 A | 4/1998 | Chung et al. | 128/633 |
| 5,769,791 A | 6/1998 | Benaron et al. | |
| 5,785,658 A | 7/1998 | Benaron et al. | |
| 5,785,704 A | 7/1998 | Bille et al. | |
| 5,799,656 A | 9/1998 | Alfano et al. | |
| 5,800,350 A | 9/1998 | Coppleson et al. | |
| 5,807,261 A | 9/1998 | Benaron et al. | |
| 5,984,861 A | 11/1999 | Crowley | |
| 6,026,331 A | 2/2000 | Feldberg et al. | |
| 6,096,065 A | 8/2000 | Crowley | |
| 6,119,031 A | 9/2000 | Crowley | |
| 6,129,667 A | 10/2000 | Dumoulin et al. | |
| 6,185,443 B1 | 2/2001 | Crowley | |
| 6,238,348 B1 | 5/2001 | Crowley et al. | |
| 6,324,418 B1 | 11/2001 | Crowley et al. | |
| 6,343,227 B1 | 1/2002 | Crowley | |
| 6,405,073 B1 | 6/2002 | Crowley et al. | |

FOREIGN PATENT DOCUMENTS

| | | |
|---|---|---|
| DE | 888727 | 7/1949 |
| DE | 30 23 130 | 1/1982 |
| DE | 40 05 743 | 8/1991 |
| DE | 195 12 518 | 10/1995 |
| EP | 0 304 321 | 9/1992 |
| EP | 0 629 380 | 12/1994 |
| EP | 0 650 694 | 5/1995 |
| EP | 0 314 937 | 10/1995 |
| EP | 0 728 440 | 8/1996 |
| EP | 0 777 119 | 6/1997 |
| EP | 0 792 618 A1 | 9/1997 |
| EP | 0 872 211 A1 | 10/1998 |
| EP | 0 920 831 | 6/1999 |
| JP | 63-167577 | 7/1988 |
| JP | 1-101965 | 4/1989 |
| JP | 1-101966 | 4/1989 |
| JP | 2-200237 A | 8/1990 |
| JP | 02-223828 | 9/1990 |
| JP | 3-159661 A | 7/1991 |
| JP | 03-264042 | 11/1991 |
| JP | 4-79931 | 3/1992 |
| JP | 61-33636 | 5/1994 |
| JP | 05-235327 | 4/1995 |
| JP | 07-88105 | 4/1995 |
| JP | 7-222712 | 8/1995 |
| JP | 7-250837 | 10/1995 |
| JP | 07-289506 | 11/1995 |
| JP | 8-64860 | 3/1996 |
| JP | 08-83569 | 3/1996 |
| JP | 8-503401 T | 4/1996 |
| JP | 8-146307 | 6/1996 |
| JP | 09-047429 | 2/1997 |
| JP | 09-080319 | 3/1997 |
| JP | 9-192138 | 7/1997 |
| WO | WO 90/04352 | 5/1990 |
| WO | WO 90/12536 | 11/1990 |
| WO | WO 91/15151 | 10/1991 |
| WO | WO 92/14514 | 9/1992 |
| WO | WO 92/15253 | 9/1992 |
| WO | WO 94/13191 | 6/1994 |
| WO | WO 95/12349 | 5/1995 |
| WO | WO 96/05693 | 2/1996 |
| WO | WO 96/07451 | 3/1996 |
| WO | WO 96/10363 A1 | 4/1996 |
| WO | WO 96/24406 | 8/1996 |
| WO | WO 96/39932 | 12/1996 |
| WO | WO 97/01985 | 1/1997 |
| WO | WO 97/06724 A1 | 2/1997 |
| WO | WO 97/22848 A1 | 6/1997 |
| WO | WO 98/22805 | 5/1998 |
| WO | WO 99/18844 A1 | 4/1999 |

OTHER PUBLICATIONS

Anidjar et al., "Ultraviolet Laser-Induced Autofluorescence Distinction Between Malignant and Normal Urothelial Cells and Tissues",

*Journal of Biomedical Optics*, vol. 1 No. 3, pp. 335-341, 1996.

Coleman et al., "Acoustic Emission and Sonoluminescence Due to Cavitation at the Beam Focus of an Electrohydraulic Shock Wave Lithotripter", *Ultrasound in Med. Biol*, vol. 18, No. 3, pp. 267-281 (1992).

Cothren et al., "Gastrointestinal Tissue Diagnosis by Laser-Induced Fluorescence Spectroscopy at Endoscopy" *Gastro Endoscopy*, vol. 36 No. 2, pp. 105-111, 1990.

Crowley et al., "Ultrasound Guided Therapeutic Catherters: Recent Developments and Clinical Results", *The International Journal of Cardiac Imaging*, vol. 6, pp. 145-156, 1991.

http://iqe.ethz.ch/'fpst/Final_Report/M4/M4PO4-1.html, Jul. 25, 1996—LESIT Final Report 1995, Module 4 Microsensor Technology (Baltes), Project 4.4: Integrated UV-Sensor by Bollinger, et al.

Huang et al., "Fluorescence Diagnosis of Gynecological Cancerous and Normal Tissues", *SPIE*, vol. 2135, pp. 42-44, 1994.

Kapadia et al, "Laser-induced fluorescence spectroscopy of human colonic mucosa", *Gastroentrerology*, vol. 29, pp. 150-157, 1990.

Ko, Biomedical Sensors and Actuators, Electronics Engineers' Handbook, McGraw-Hill 1989, pp. 26-53-26-68.

Kopp et al., "Stay Tuned: Photonic Filters Color Your World", *Photonics Spectra*, Mar. 1997, pp. 125-129.

Lilge et al., "Light Induced Fluorescennce Spectroscopy at Endoscopy", *Presented at the 10th Asisan Pacific Congress of Gastroenterology*, 1996.

Meindi, J. Implantable Telemetry in Biomedical Research, Electronics Engineers' Handbook, McGraw-Hill 1989, pp. 26-41-25-53.

Petrofsky, "In Vivo Measurement of Brain blood Flow in the Cat," *IEEE Transaction on Biomedical Engineering BME-26*(8):441-445 (Aug. 1979).

Vona et al., "A Test of the Hypothesis that Cavitation at the Focal Area of an Extracorporeal Shock Wave Lithotripter Produces Far Ultraviolet and Soft X-Ray Emissions", *J. Acoust. Soc. Am.*, vol. 98 (2), pp. 706-711, (Aug. 1995).

International Search Report for PCT/US97/20367 dated Mar. 23, 1998.

International Search Report for PCT/US97/20324 dated Mar. 11, 1998.

International Search Report for PCT/US97/20435 dated May 19, 1998.

International Search Report for PCT/US98/20019 dated Jan. 20, 1999.

International Search Report for PCT/US98/20018 dated Jan. 21, 1999.

International Search Report for PCT/US98/21100 dated Feb. 8, 1999.

* cited by examiner

MINIATURE SPECTROMETER

CROSS-REFERENCE TO RELATED APPLICATION

This application is a continuation of U.S. patent application Ser. No. 09/478,774 filed Jan. 6, 2001, which is a continuation application of U.S. patent application Ser. 08/898,604 filed Jul. 22, 1997, now U.S. Pat. No. 6,119,031 which is based on U.S. provisional application Ser. No. 60/033,334 filed Nov. 21, 1996. The entire disclosure of these applications are incorporated herein by reference.

TECHNICAL FIELD

This invention relates to a spectrometer and, more particularly, to a miniature spectrometer for placement within a body for tissue characterization.

BACKGROUND INFORMATION

Spectral analysis of living tissue can be used to detect various forms of cancer and other types of diseases. In spectral analysis, light illuminates tissue region under examination and a light detector detects optical properties of the illuminated tissue region by measuring light energy modified by its interaction with the tissue region in a pre-determined frequency and amplitude domain. Optical properties include absorption, luminescence, fluorescence, frequency and time-domain responses to various materials injected to the tissue region and other electromagnetic responses. Diseased tissue may be identified by comparing a spectrum obtained to spectra of normal tissue obtained under the same controlled conditions.

Current devices available for tissue characterization using spectral analysis include night vision sensing systems with filtering adapted to be used with endoscopes and multichannel fiber optic delivery systems. The latter systems typically include a light source, an optical conduit, a light applicator and receiver, a second light conduit, a spectrometer and a display unit. These systems tend to be very expensive, to require large accompanying electronic systems, and to be complex requiring operator training.

The optical fibers used as optical conduits in the multichannel fiber optic delivery systems are source of design difficulties. In order to transport an adequate amount of light energy from the light source to a tissue region inside a body, a significant amount of optical fibers must be included in an interventional device. An interventional device, such as a catheter, however, does not include a lot of space and higher quality optical fibers, which take up less space, are expensive.

Optical fibers also lack mechanical properties necessary to be used with an interventional device. Optical fibers can break when flexed and have a relatively high stiffness compared to conventional catheter materials. Therefore, it is difficult to design a flexible tip for a catheter, which includes optical fibers and overall flexibility of an interventional device which include optical fibers is limited.

Furthermore, optical fibers require an expensive terminating connector and must be properly coupled to afford adequate light throughput. Signal efficiency of fiber based devices depends greatly upon the devices' ability to couple sufficient light into the fibers at the desired wavelength. For spectral analysis, filtered broadband light sources are preferred over laser light sources for cost and frequency versatility. However, it is a challenge to efficiently couple light from a lamp source into fibers with small diameters. Although laser light is more easily coupled into optical fibers, laser light sources are generally more expensive, are obtainable in only a few selected wavelengths, and are subject to more critical regulatory controls than other light sources. Furthermore, light emitted by the subject illuminated by a laser light tends to be weak and is also subject to all of the loss mechanisms and inefficiencies problematical to a laser system.

Additional hardware, such as connectors and couplers, and the need to provide one or more optical conduits along the length of the interventional device, make conventional devices used for spectral analysis relatively expensive, inconvenient, and perhaps impractical.

SUMMARY OF THE INVENTION

In one aspect, the invention features a miniature spectrometer for use in spectral analysis. The spectrometer includes a light source and a light detector for placement inside a body such that optical conduits are not necessary to deliver light signals to and from tissue inside the body. The miniature spectrometer includes the light source and one or more light detectors. The light source illuminates a tissue region and the light detectors detect optical properties of the illuminated tissue by measuring modified light signals. The light detectors convert optical signals to electrical signals such that one or more electrical wires placed inside an interventional device can deliver the electrical signals from the tissue to a signal display or a microprocessor.

Embodiments of this aspect of the invention include the following features. The light source and the light detectors are energized by an external power supply through electrical wires. In another embodiment, an optically transparent tip encapsulates a spectrometer. The tip is shaped to optimize tissue contact and optical transmission. The tip encapsulating the spectrometer is disposed at a distal end of an interventional device. The tip may be coated with a material to improve light transmission. The tip may include at least one fluid channel, which is in communication with a lumen inside the interventional device, to deliver a fluid to a tissue region. In one disclosed embodiment, a spectrometer of the invention includes a light source and the light detectors formed on a single substrate. The light source may be a light emitting diode and the light detectors may be a photodiode comprising multiple channels, where both devices are formed on a silicon substrate. The light detector can include multiple channels to detect light emission at multiple wavelengths.

In another aspect, the invention features a method for characterizing tissue. According to the method, a spectrometer which includes a light source and a plurality of light detectors is provided. The spectrometer is placed inside a body near a tissue region to be characterized. The light source and the detectors are connected to a power source through electrical wires. The energized light source generates light and illuminates the tissue region. The detectors measure light signals modified as a result of interacting with the tissue region. The light detectors convert received optical signals to electrical signals. In one embodiment of this aspect of the invention, an optically transparent tip encapsulates the spectrometer and is located near a distal end of an interventional probe. The method can further include the step of rotating the spectrometer with respect to the tip. The rotation adjusts optical properties of the light transmitted to illuminate the tissue.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1A:
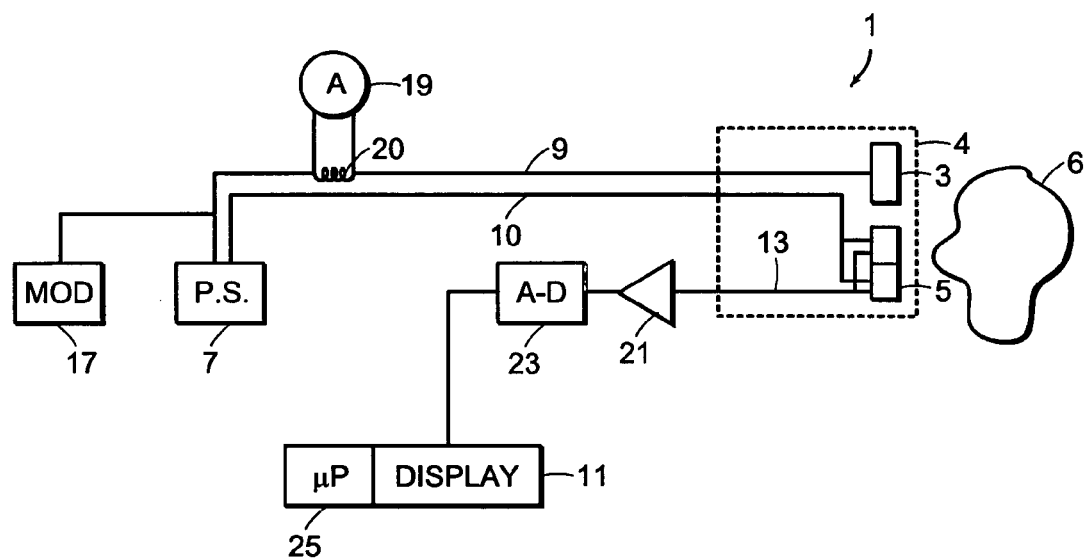
FIG. 1A is a block diagram of a system for spectral analysis including a spectrometer module in communication with external components.

Referring to FIG. 1A, the spectrometer module 1 includes a light source 3 and a multichannel light detector 5 in close proximity to each other and to a region of interest 6. The region of interest 6 may be living tissue located inside a body. The light source 3 and the light detector 5 are located in close proximity to the region of interest so that they may both emit and/or couple the light energy efficiently with minimum intervening space or material. The light source 3 is in communication with a power supply or source 7 through a DC power line 9, and the light detector 5 is in communication with the power source 7 through a bias supply line 10. The power source 7 may provide direct current (DC) of either high or low voltage, alternating current (AC) of an appropriate frequency, or a pulse. AC power may be supplied to the light source 3 for the purpose of modulating the light source with a modulator 17. Alternatively, current with complex waveforms may be supplied to the light source 3. A diode may be placed in the circuit at the light source 3 to rectify some of the AC power so that it can be used to bias the detector 5. In the disclosed embodiment, a metering device 19 is placed at the source of power and employs a current sampler 20 in line to monitor and display the power applied to the light source 3. This configuration may be used to help calibrate the instrument during use.

One or more output lines 13 extend from the detector 5 to a microprocessor 25 and a display 11 through an amplifier 21 and an A-D converter 23. The output lines 13 may be shielded to reduce noise pickup. The output of the detector 5 is amplified through an amplifier 21 and sent to an analog-to-digital (A-D, A/D, or A-to-D) converter 23. The digitized signal can then be sent to a microprocessor 25 or other logical device for subsequent spectral analysis. An alternative signal processing system is shown in FIG. 1B.

Figure 1B:
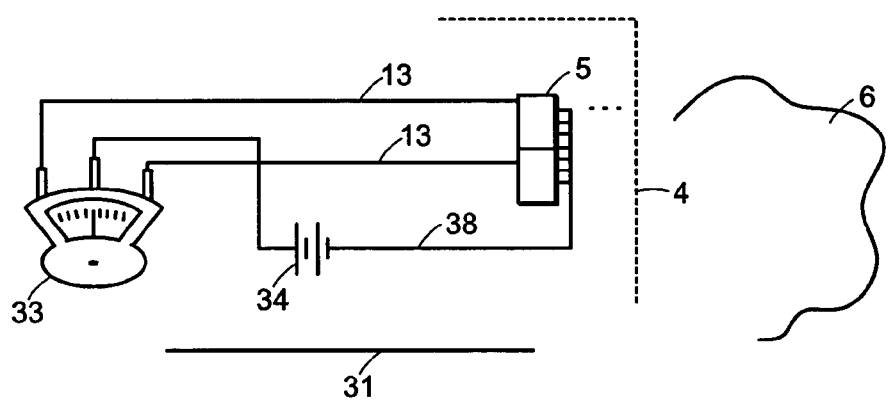
FIG. 1B shows a light detector of the spectrometer module of FIG. 1A in communication with an alternative electronic system for signal analysis.

Referring now to FIG. 1B, the alternative signal processing system includes a centering scale meter 33 driven by a DC source 34 placed in the common return line 38 extending from the light detector 5. This alternative signal processing system may be used to observe the different signal amplitudes of optical signals received by two or more channels of the light detector 5 operating simultaneously, or the normalized output of the light source versus the light energy received by the light detector 5. The amplitude of the reading may be used to determine the slope of the response signal relative to the input signal or to perform other more complex functions. It should be understood at this point that an equivalent operation may be obtained using a single channel light detector as long as a response property of the channel is varied over time. It may be possible to vary the response property by using, for example, one or more filters. In the case of a single channel light detector, the two signals may be obtained sequentially, if desired. The functions provided by the above-described circuitry may be achieved with other or additional electrical, mechanical, and/or optical apparatus without departing from the spirit and scope of the invention.

Figure 2A:
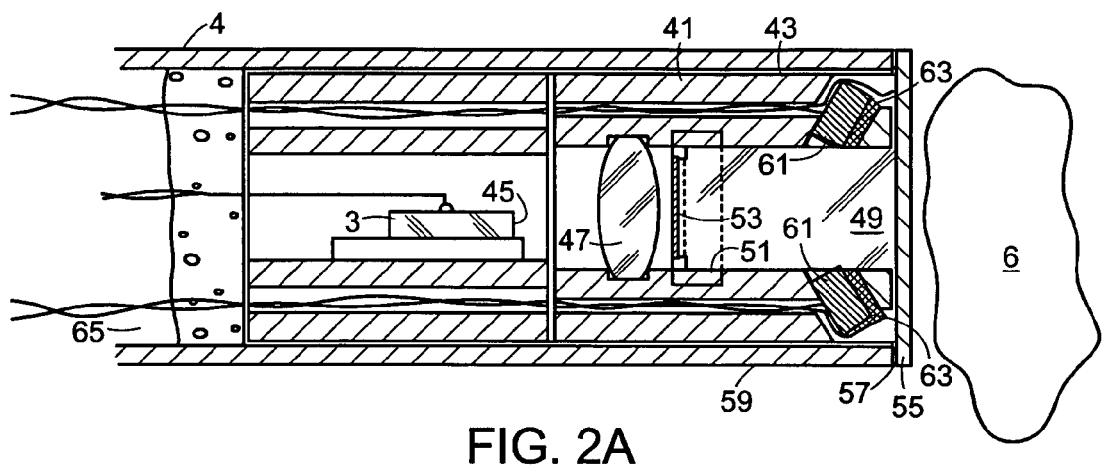
FIG. 2A is a view in cross-section of a spectrometer module disposed at a distal end of an interventional device, the cross-section being along line 2A-2A of FIG. 2B.
Figure 2B:
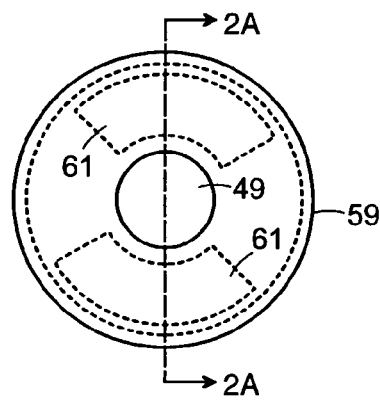
FIG. 2B is a view in cross-section of the distal end of the spectrometer module of FIG. 2A.

Referring to FIGS. 2A and 2B, a spectrometer module 41 is disposed at a distal tip of an interventional device 4. The spectrometer module 41 is placed inside a housing 43. The housing 43 comprises an optically transparent material. The diameter of the housing 41 is small enough to allow the spectrometer module 41 and the housing 43 to pass through various lumens of catheters and body lumens such as vascular and nonvascular vessels. For example, the housing 43 for a spectrometer module 41 used with a catheter 4 has a maximum diameter of about 0.25 inches. The housing 43 for a spectrometer module 41 used with a guidewire-sized device may have a maximum diameter of about 0.081 inches.

The spectrometer module 41 includes a light source 3, two light detectors 61, a lens 47, a light amplifier 49, and a window 55. The light source 3 is a semiconductor diode source, mounted such that the output end 45 is facing the distal end of the module 41, which is generally in line with the central axis of the interventional device 4. Alternatively, the light source 3 may be positioned such that the output end faces a direction transverse to the center axis of the interventional device 4. Light generated by the light source 3 may directly illuminate a tissue region or may be focused by a lens 47 before illuminating the tissue region. The lens 47 may be shaped to focus the light into a desired pattern, or may be used to diffuse the light if needed. A frequency multiplier 49 is placed in the path of light generated by the light source 3 to amplify the frequency of the light output. The frequency multiplier 49 comprises an optically nonlinear substance. The optically nonlinear substance 49 is held in position with a ring holder 51, to maintain its position with respect to the position of the light source 3. Alternatively, the nonlinear substance 49 may be bonded directly to the output end 45 of the light source 3 using an optically clear bonding material. The optically clear bonding material may be epoxy, cyanoacrylate, or sodium silicate. The bonding material may be placed directly upon the output end 45 of the light source 3 and its surrounding area, and the nonlinear substance 49 may be placed upon the bonding material. An example of an optically nonlinear substance suitable for use with a spectrometer module of the invention is a potassium dihydrogen phosphate ($KH_2PO_4$) or KDP crystal. In order to improve light transmission, at least one surface of the KDP crystal may be coated with a fluoride layer that acts as a one-quarter wave matching layer 53. A window 55 is placed at the distal end of the spectrometer module 41 to protect the module. The window 55 may be held in place by bonding the window 55 to the distal tip of the interventional device with an adhesive 57. In a preferred embodiment, the window 55 includes a bandstop filter characteristic that attenuates output frequencies of the light generated by the light source 3 while permitting passage of light output having a predetermined frequency. Light output permitted to pass through the filter is often in the ultraviolet range, and particularly has wavelengths from about 300 nm to about 400 nm. Such filters are generally available and known. Examples of these types of filters include tinted glass, sandwiched dyes, and interference filters otherwise known as dichroic filters. Alternatively, variable filtration may be employed by rotating the inner portion of the module 41 relative to portions of another colored material, such as a tinted plastic catheter sheath or a tip 81 shown in FIG. 4. The catheter sheath or the tip 81 may have differing filter characteristics owing to changes in thickness, or due to localized dyes.

One or more light detectors 61 and filters 63 may be disposed around the nonlinear substance 49 (FIG. 2B). The light detectors 61 may be, for example, silicon photodiodes, cadmium sulfide slabs with electrodes, charge-coupled devices, or generally any light sensors that may be miniaturized and placed within the confines of a device smaller than about 0.250 inches or less in diameter. The light detectors 61 may be positioned at an angle (FIG. 2A) to aid in the collection of light emitted by the region of interest 6. Alternatively, the light detectors 61 may be disposed on a flat substrate adjacent to the lightsource 3. The light signals illuminating the region of interest are modified as a result of interacting with the region of interest 6. The light detectors 61 detect the modified light signals. The light detectors 61 may also monitor light emission from the light source. The light detectors 61 are energized with the energy from the power supply 7 through a power line 10 (FIG. 1A). Frequency selective detectors 61 are produced by disposing filters 63 on the light detectors 61. The filters 63 attenuate one or more frequency bands of energy received by the light detectors 61. Filters 63, for example, may be of the bandpass type admitting wavelengths selectively. A specific bandpass of one filter may be centered around 380 nm, while another filter may be centered around 440 nm. Signal wires 13 delivering signal output may be in the form of twisted pairs of wires or may share a common ground path. The signal wires 13 are threaded through one or more lumens 65 of the interventional device 4, and extend back to a suitable connector located on or near the proximal end of the interventional device 4.

Figure 3:
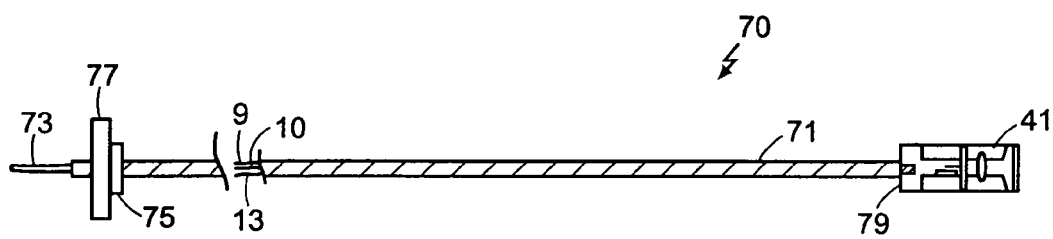
FIG. 3 is a schematic diagram of an interventional device and a spectrometer module disposed at the distal end of the interventional device.

Referring to FIG. 3, the spectrometer module 41 of FIG. 2A is disposed at the distal end of an interventional device 70. In the disclosed embodiment, the module 41 is attached to the distal end of a shaft 71, and the shaft 71 houses signal wires 9, 10, and 13. The shaft 71 terminates with a small connector 73 at the proximal end. The connector 73 may have one or more contacts arranged to permit electrical, optical, and mechanical connection to a mating connector. The shaft 71 also has a slidable stop 75 that may be prepositioned to allow control of the depth of placement within the body. The stop may be a collar with a collet ring 77 that tightens when twisted to provide a positive stop. The shaft 71 may comprise a tube, such as stainless steel hypo tube, superelastic (nitinol) tube, or the like. The advantage of such shafts is that they are relatively rigid and allow insertion into partly occluded passages. Very small shafts may be made with metal tubes. Shafts having outside diameters of about 0.005 inches may be provided, although in most instances, larger shafts with diameters of about 0.08 inches or larger are adequate. Lengths of the shafts may also vary between a few millimeters to over 200 centimeters. The shaft 71 may be made of a more flexible material if desired. Multi-layered counterwound wires of small diameter may be used as the shaft material. These shafts have relatively high lateral flexibility and good torsional stiffness, and can be positioned to specific angles by manual twisting or by a motor. Other shafts may be comprise plastics such as polyethylene, polyimide, or nylon and may have one or more lumens. Lumens carry electrical, optical or mechanical transmission lines, or cooling fluids. In the disclosed embodiment, the shaft 71 has a screw thread 79 at the distal end to facilitate attachment and detachment of the module 41 to the shaft 71. One possible use of the attachment thread may be to release the module 41 from the end of the shaft 71, once the module 41 is positioned inside a body, by unscrewing and releasing the module 41. The tubular shaft 71 may then slide over the small connector 73, which may be left outside the body. The module 41 may be re-connected to the shaft 71 before withdrawing the module 41 from the body.

Figure 4:
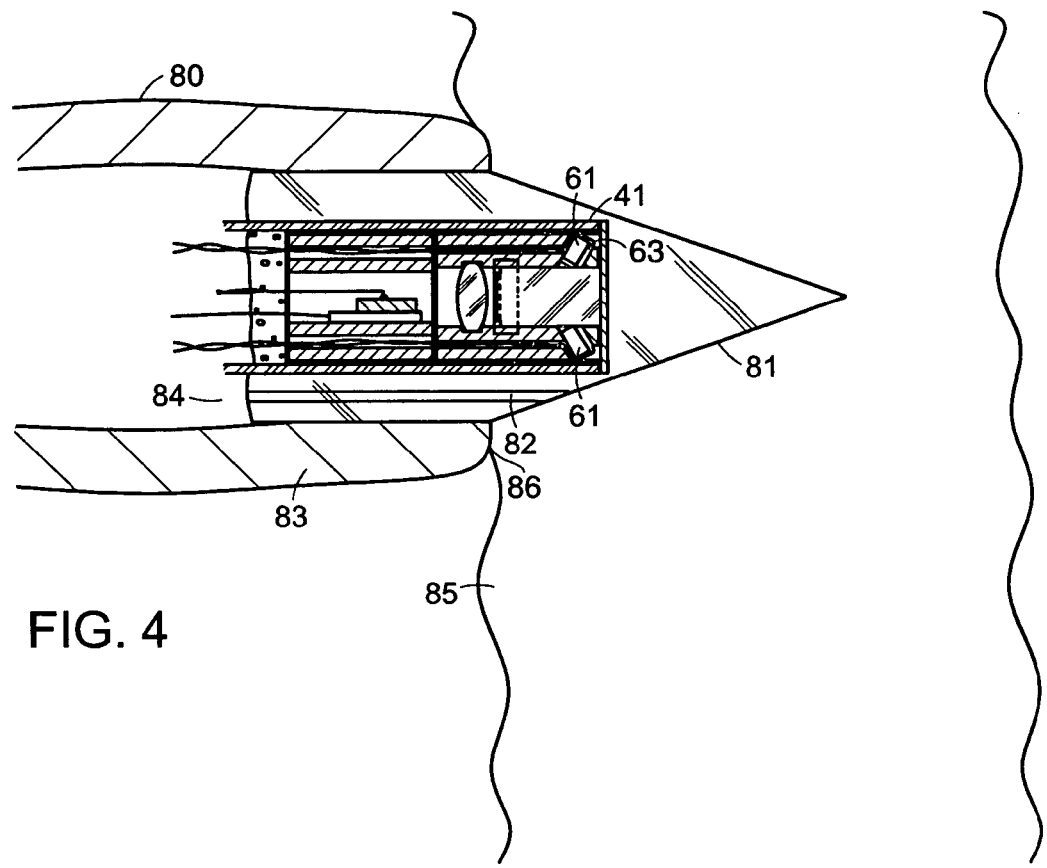
FIG. 4 is a view in cross-section of the spectrometer module of FIG. 2A encapsulated by a tip and disposed at the distal end of an interventional device.

Referring to FIG. 4, the spectrometer module 41 of FIG. 2A is located inside an optically transparent tip 81, and the tip 81 and the module 41 are disposed at the distal end of an interventional device 80. The tip 81 may comprise a plastic such as polystyrene, a glass such as quartz, or alternatively be molded out of a dissolvable material such as sucrose. The tip 81 includes a fluid channel 82 that is in communication with the central lumen 84 of the catheter body 83. The fluid channel 82 may be used to provide a coupling fluid such as water at or near the tip of the device, or to inject a dye (such as india ink) or a drug (such as Photofrin), or to collect a sample of fluid or tissue. The tip 81 may include secondary filters 87. Positioning the module 41 relative to the tip 81 allows variations in the optical pathway to be obtained. For instance, the module 41 may be rotated within the tip 81, such that secondary filters line up with one or more of the detectors 61 or light emitted from the light source 3.

A catheter body 83 may house the module 41, by passing the module through the central lumen 84 of the catheter 83, to guide the module 41 to the region of interest in mucosal tissue 85. The embodiment shown in FIG. 4 allows the operator to monitor a change in the tissue as a result of a drug injections, or the selective uptake of a fluorescent dye. The shape of the tip 81 aids in the avoidance of specular reflections of light from the surface of the mucosal lining 85 and the displacement of intervening materials such as bacteria which often strongly fluoresce. The tip 81 can essentially provide angle independence, while avoiding the need for actual removal of tissue material. If the tip 81 is slightly rounded, displacement of tissue is accomplished without actually shearing the tissue significantly. Penetration depth may be controlled by placing the shoulder 86 of the catheter 83 against the tissue and sliding the tip 81 relative to the catheter 83. Ranges of extension from flush or negative clearance to about 1.0 mm or greater protrusion of the tip 81 beyond the shoulder 86 are practical using a friction fit between the two components. The shaft 71 (FIG. 3) and the module 41 may be bonded to the tip 81 if desired with clear epoxy. The advantage of such configuration is that the entire assembly may be slidably and rotatively positioned within catheter 83. The tubular form of catheter 83 is merely exemplary. Numerous catheter sheaths and other interventional devices that are used to conduct fluids may be used including needles, guidewires, guiding catheters, trocars, introducers, endoscopes, and stents.

The tube or the housing may be filled with an optically transparent material or a diffusing material. Examples of optically transparent material include epoxy, water, and oil. Examples of diffusing material include particulate matter suspended in a viscous fluid, like an epoxy which may harden or an elastomeric material which may remain flexible to conform to various anatomical conditions or be shaped into various catheter tips.

Figure 5:
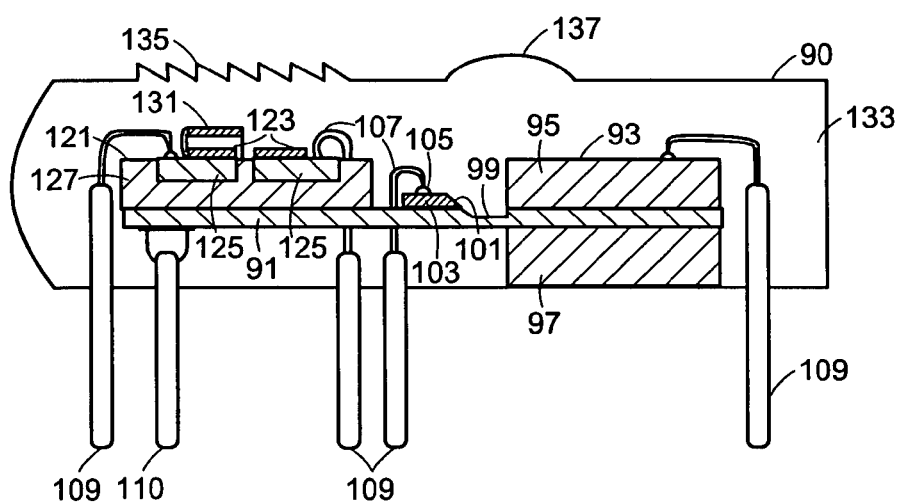
FIG. 5 is a view in cross-section of a single substrate spectrometer module, the cross-section being along the length of the module.

The interventional device of FIG. 4 may be made more useful, less expensive, and smaller by incorporating all of the functional elements into a single substrate which may be embedded, attached, disposed or implanted in interventional devices and living tissue at will. In FIG. 5, a single substrate spectrum analysis package 90 employs these features in such a compact arrangement. In the disclosed embodiment, the elements are formed on a doped, layered silicon substrate.

Alternatively, the substrate 91 may be an etched printed circuit on an epoxy fiberglass resin substrate. The light emitting portion is an integral light emitting diode arrangement 93 including etched semiconductor N material 95 and a diamond heat sink 97 bonded to one side of the substrate 91. The gap 99 etched below the reference surface of the substrate 91 allows light energy to be directed to the mirror 101, which is bonded to the piezoelectric light modulator 103. The mirror 101 may be constructed by aluminizing a portion of the piezoelectric light modulator 103 after beveling and polishing the modulator 103. Alternatively, the mirror may include a small slab of glass material, about 0.150 mm square and 0.010 mm thick, bonded with a thin layer of epoxy resin to stack actuator in a position that allows clearance within the gap 99. The construction of the piezoelectric light modulator 103 may be accomplished by bonding a single layer of Lead Zirconate-Titinate (PZT) directly to the substrate 91 using a conductive epoxy and ultrasonically welding or epoxy bonding an electrode 105 with a fine copper wire 107, which is in turn bonded to an electrical terminal post 109. The terminal posts 109 can be about 0.030 mm in diameter and about 0.328 mm in length, and they can comprise brass wires plated with gold. A large post 110 is welded ultrasonically to the base of substrate 91 and serves as an orientation key, a mechanical stabilizer, and is also capable of carrying somewhat higher current.

Also etched from the substrate 91 is an avalanche photodiode (APD) array 121, which serves as a very sensitive light detector. In the embodiment shown in FIG. 5, the light detector 121 has a two channel version. More channels, however, may be added by simply repeating the structure as follows: deposit Silicon oxide ($SiO_2$) layers 123 on N material layers 125, which are individually connected to posts 109 through fine wires 107. The depletion layer 127 is sandwiched between the N material layers 125 and the substrate 91, and may also serve as part of the common return circuit to post 110. A colored light filter 131 may be positioned over one or more of the light sensitive portions of the APD such that the spectral response of one channel is different from that of the other. In the disclosed embodiment, a colored light filter 131 is positioned over one channel. The filter, for example, may comprise a wave filter such as a dichroic filter made of a glass, a grating, or a dye. The filter 131 may be temporarily positioned over a silicon oxide layer 123 and held in place while optical potting plastic 133 is molded over the assembly. Materials such as polystyrene, polycarbonate and methyl-methacrylate, for example, may be used as the optical potting plastic to cast or injection mold a desired shape of the package 90. Other materials such as urethanes may be used to form the cast as long as they are sufficiently transmissive of light energy and are reasonably elastic to allow small excursion such as the mirror 101. An air space around the gap 99 may be desirable depending on the index of refraction needed in the vicinity of the mirror 101 and the output end of the light emitting diode 93. One way to accomplish this is to place a premolded frame over the gap 99, which prevents the flow of potting material into that area. The frame may be injection molded out of the material also being used for the package 90 or a material that has a higher melting temperature. The frame may be bonded in place with a thin layer of clear epoxy film. The package 90 may be shaped to permit modification of the optical signals, which may enter or exit the package. In the embodiment shown, the serrated lens 135 is molded or embossed into the surface of the package 90. The advantage of this configuration is that a polished mold may be used to form a precision optical surface as desired. The state of the art injection molding techniques and relatively low viscosity thermoplastics such as polystyrene allow creation of very fine features with controllable dimensions and step heights on the surface. A dimension of the surface feature may be in the range of about 0.005 mm. Even finer features of less than 0.005 mm may be embossed using pressure and a photo-etched master such that binary optical steps, holograms, or gratings capable of diffracting IR, visible, and UV light may be formed directly on the surface of the package 90. Creation of such features on the surface, or within the assembly, avoids the need for additional, expensive optical components and their holders. A conventional curved lens 137 is created on the surface of the package 90 to focus the light energy as desired. The conventional curved lens 137 also may be molded to the surface during the molding operation. A grating may disperse light across the one or more detectors providing frequency selection capability.

Spectrometer modules according to the invention are designed to place the light source and the light detector in proximity to a tissue region under spectral analysis. Tissue characterization using spectral analysis is based on the understanding that light emitted from a light source interacts with the tissue and modifies the light. Absorption, scattering, and other loss of energy occurs when light interacts with the tissue. Various tissue types, however, have differing absorption and reflection properties. Therefore, tissue can be characterized using spectral analysis. These interaction phenomena, however, also limit the depth of light penetration that can be achieved. Therefore, energy loss due to extraneous factors may be severe when the light source is not located near the tissue of interest. The invention provides means for placing the light source and the light detector near the tissue of interest, such that efficient operation can be achieved. Therefore, the spectrometer module of the invention eliminates unnecessary light loss and allows the light detector to detect light modification caused by the interaction with the tissue.

In general, any type of light detector capable of detecting modified light signals due to its interaction with the subject under analysis and capable of being made sufficiently small to fit in an interventional device may be used in accordance with the invention. For example, a charge coupled device (CCD) sensor may be arranged circumferentially around the energy generating source and connected via signal wires. Alternatively, silicon photodiodes, cadmium sulfide cells or scintillation detectors may be arranged such that a returning portion of the lightwave energy is captured and measured. In the case of CCD type sensors, a large number of such devices may be incorporated in a very small area, although only one such sensor may be necessary to obtain and measure a useful signal. Alternatively, two or more sensors may be used in accordance with the invention. The advantage of using multiple sensors is that it eliminates the need for changing filters. Filter x for instance, may be arranged to admit blue lightwaves, while filter y may be arranged to admit red lightwaves, such that the relative intensity of two wavelengths can create a slope which may indicate a particular tissue type or state.

Any light source capable of being placed in an interventional device may be used according to the invention. An ordinary incandescent light source such as a tungsten filament light source with appropriate filtering disposed thereon, an arc lamp, a mercury vapor lamp, a xenon flash lamp, gas discharge tubes filled with various gases, metallic vapors, an acoustically driven sonoluminescent source capable of generating visible and UV light, and X-rays, a Gunn diode source of super high frequency energy (SHF), light-emitting diodes, and other light sources capable of either long or short duration output, at long or short wavelengths may be used with the invention.

Possible light source systems and light detection arrangements are described in two commonly-owned U.S. provisional patent applications, namely U.S. provisional patent application Ser. No. 60/033,333 and U.S. provisional patent application Ser. No. 60/033,335. These disclosures, and any regular U.S. patent applications converted on the basis of one or both of these provisional applications, are hereby incorporated herein by reference. In general, a light source system and a light detection system are selected for use according to the invention based on various factors including, for example, cost, complexity, miniaturization, and therapeutic properties.

The shape of the spectrometer module of the invention may be any form suitable for optimizing the contact between the module and the region of interest or optical transmission of generated light to the region of interest. Possible shapes include, for example, concave, stepped, cylindrical, chisel tipped, conical, convex, and hemispherical. In addition, the outer or inner surface of the module may be coated with a special material to enhance the light transmitting properties or be provided with a microlens, a binary optical step, or a wavelength filter.

Although the invention has been described in terms of both the light source system and the light detector system, it should be understood by those skilled in the art that the light source system alone and the detector system alone may be used in certain circumstances where the need arises. Furthermore, it should be understood that either the light source or the detector may be substituted with a non-light generating or receiving device. Examples include radiofrequency generating and receiving systems capable of spectroscopy at longer wavelengths, and x-ray generating and receiving systems capable of x-ray spectroscopy. In general, some of the basic features of the invention include generating a local energy source, applying the energy source to a selected area of tissue, and collecting energy which has been modified by interaction with the selected area of tissue. The collected energy signals preferably are analyzed to characterize the tissue, and the results indicated to an operator or user.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A tissue spectroscopy device comprising:
   a substrate having a light emitting portion at a distal end of a first surface thereof, the light emitting portion providing only ultraviolet (UV) light to tissue, and a light detector disposed at a proximal end of the first surface; and
   an interventional device for delivering the substrate to a target position adjacent to a target portion of tissue within a living body.

2. The device of claim 1 further comprising a filter associated with said light detector permitting only a desired portion of the light incident thereon to pass therethrough.

3. The device of claim 2 wherein said filter is a bandpass filter centered around 380 nm.

4. The device of claim 2 wherein said light detector comprises a first channel and a second channel and wherein said filter is disposed on said first channel.

5. The device of claim 1 wherein said light emitting portion comprises a light emitting diode.

6. The device of claim 5 wherein said light emitting portion further comprises a lens.

7. The device of claim 5 wherein said light emitting portion further comprises a filter, said filter permitting light output only within the UV range.

8. The device of claim 1 wherein the substrate further comprises a heat sink disposed on a second surface thereof, the second surface being opposite said first surface.

9. The device of claim 1 wherein the substrate further comprises a light modulator disposed on said first surface, a mirror disposed on said light modulator at an angle selected to receive light emitted by said light emitting portion, and an etched gap between said light modulator and said light emitting portion.

10. The device of claim 1 wherein said substrate comprises doped silicon.

11. The device of claim 1 wherein said light detector comprises an avalanche photodiode array.

12. The device of claim 1 wherein said distal end further comprises a substantially transparent window.

13. The device of claim 12 wherein said window comprises a material selected from a group consisting of polystyrene, polycarbonate, and methyl-methacrylate.

14. The device of claim 1 further comprising an optical device selected from the group consisting of a lens, a filter, a mirror, a frequency multiplier, a binary optical step, a grating, and a hologram.

15. The device of claim 14 wherein said filter is serrated.

16. A method for characterizing a tissue, said method comprising the steps of:
   (a) delivering to a desired position adjacent to target tissue within a living body a substrate comprising a light emitting portion at a distal end of a first surface thereof and a light detector disposed on a proximal end of the first surface;
   (b) transmitting only ultraviolet (UV) light from said light emitting portion to illuminate said target tissue; and
   (c) using said light detector to measure an optical property of light reflected from the target tissue.

17. The method of claim 16, wherein step (c) comprises using a filter to filter out non-targeted portions of light received by said detector.

18. The method of claim 17, wherein said light detector comprises a first channel and a second channel and wherein said filter is disposed on said first channel.

19. The method of claim 16 wherein the light emitting portion comprises a light source and a filter, and said step (b) comprises using said filter to permit only light in the UV range to be transmitted to the target tissue.

20. The device of claim 7 wherein said filter permits output of all wavelengths between about 300 nm and 400 nm.

* * * * *